US00PP30585P2

(12) United States Plant Patent
Clark

(10) Patent No.: US PP30,585 P2
(45) Date of Patent: Jun. 18, 2019

(54) COLEUS PLANT NAMED 'UF16-88-9'

(50) Latin Name: *Plectranthus scutellarioides*
Varietal Denomination: UF16-88-9

(71) Applicant: Florida Foundation Seed Producers, Inc., Marianna, FL (US)

(72) Inventor: David G. Clark, Gainesville, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 15/732,778

(22) Filed: Dec. 27, 2017

(51) Int. Cl.
*A01H 5/12* (2018.01)

(52) U.S. Cl.
USPC ..... Plt./469
CPC ..... *A01H 5/12* (2013.01)

(58) Field of Classification Search
USPC ..... Plt./469
See application file for complete search history.

(56) References Cited

U.S. PATENT DOCUMENTS

PP27,288 P3 10/2016 Clark et al.
PP27,499 P2 12/2016 Clark et al.

*Primary Examiner* — Anne Marie Grunberg
(74) *Attorney, Agent, or Firm* — Dentons US LLP

(57) ABSTRACT

'UF16-88-9' is a new *Coleus* plant with novel characteristics that include a vigorous compact mounded growth habit, an excellent heat tolerance, and consistent maroon leaves with bright pink centers. It has superior stability in foliage color in both sun and shade conditions, maintaining stable color in all conditions. 'UF16-88-9' has not been observed to produce flowers in any trial we have conducted to date, and thus it has long season performance as an annual plant in the landscape until late Fall.

3 Drawing Sheets

Latin name of the genus and species of the plant claimed: *Plectranthus scutellarioides.*

Cultivar denomination: 'UF16-88-9'.

BACKGROUND OF THE INVENTION

The invention relates to a new and distinct cultivar of *Coleus* plant named 'UF16-88-9'. 'UF16-88-9' originated from an open-pollination conducted in May-November 2015 in Gainesville, Fla. between the female *Coleus* plant 'UF15-76-1' (unpatented) and an unknown male *Coleus* plant. A single seedling was chosen in May 2016 for further asexual propagation in Gainesville, Fla.

'UF16-88-9' has been reproduced asexually for over 18 months through vegetative cuttings and has been found to retain its distinctive characteristics through successive asexual propagations. 'UF16-88-9' was first propagated asexually by meristem tip cuttings in May 2016 in Gainesville, Fla., and has remained true-to-type since that time.

'UF16-88-9' has maroon lance-shaped leaves with deep pink centers that are much longer than they are wide; whereas, 'UF15-76-1,' the female parent, has lance-shaped leaves that are colored deep maroon with green accents. 'UF16-88-9' has an extremely vigorous well-branched mounded habit; whereas 'UF15-76-1' is vigorous, but more upright in habit with less lateral branching.

'UF16-88-9' has similar maroon and pink foliage color to the commercial variety Velveteen® ('UF13-6-11,' unpatented), but 'UF16-88-9' is not as upright and rangy in habit. 'UF16-88-9' has lance-shaped leaves and mounded habit similar to the commercial varieties 'UF12-82-3' (U.S. Plant Pat. No. 27,288) and 'UF12-73-5' (U.S. Plant Pat. No. 27,499); however, 'UF12-82-3' and 'UF12-73-5' do not have the maroon and pink foliage color of 'UF-16-88-9.'

SUMMARY OF THE INVENTION

The following are characteristics of 'UF16-88-9' when grown under normal horticultural practices in Gainesville, Fla. 'UF16-88-9' has a novel, vigorous, compact upright growth habit, an excellent heat tolerance, and consistent maroon and bright pink lance-shaped leaves that are significantly different than other *Coleus* plants. It has superior stability in foliage color in both sun and shade conditions, maintaining stable color in all conditions. When 'UF16-88-9' is grown as a stock plant, it has a vigorous but compact upright growth habit with excellent lateral branching, and thus provides ample vegetative propagules for producers. 'UF16-88-9' has not been observed to produce flowers in any trial we have conducted to date in Gainesville, Fla., and thus it is desirable for long-season performance in the landscape.

BRIEF DESCRIPTION OF THE DRAWINGS

This new *Coleus* plant is illustrated by the accompanying photographs, which show the plant's form and foliage. The colors shown are as true as can be reasonably obtained by conventional photographic procedures. The photographs in FIGS. 2 and 3 are of plants grown for 11 weeks from unrooted cuttings in May-July 2017 in a poly-covered plastic greenhouse in Gainesville, Fla.

DETAILED BOTANICAL DESCRIPTION

Figure 1:
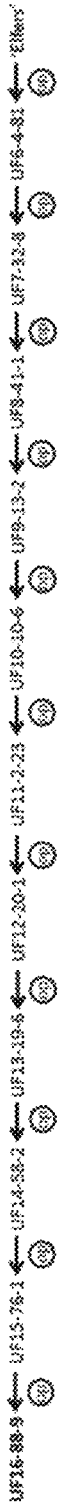
FIG. 1—Shows the pedigree of 'UF16-88-9.'
Figure 2:
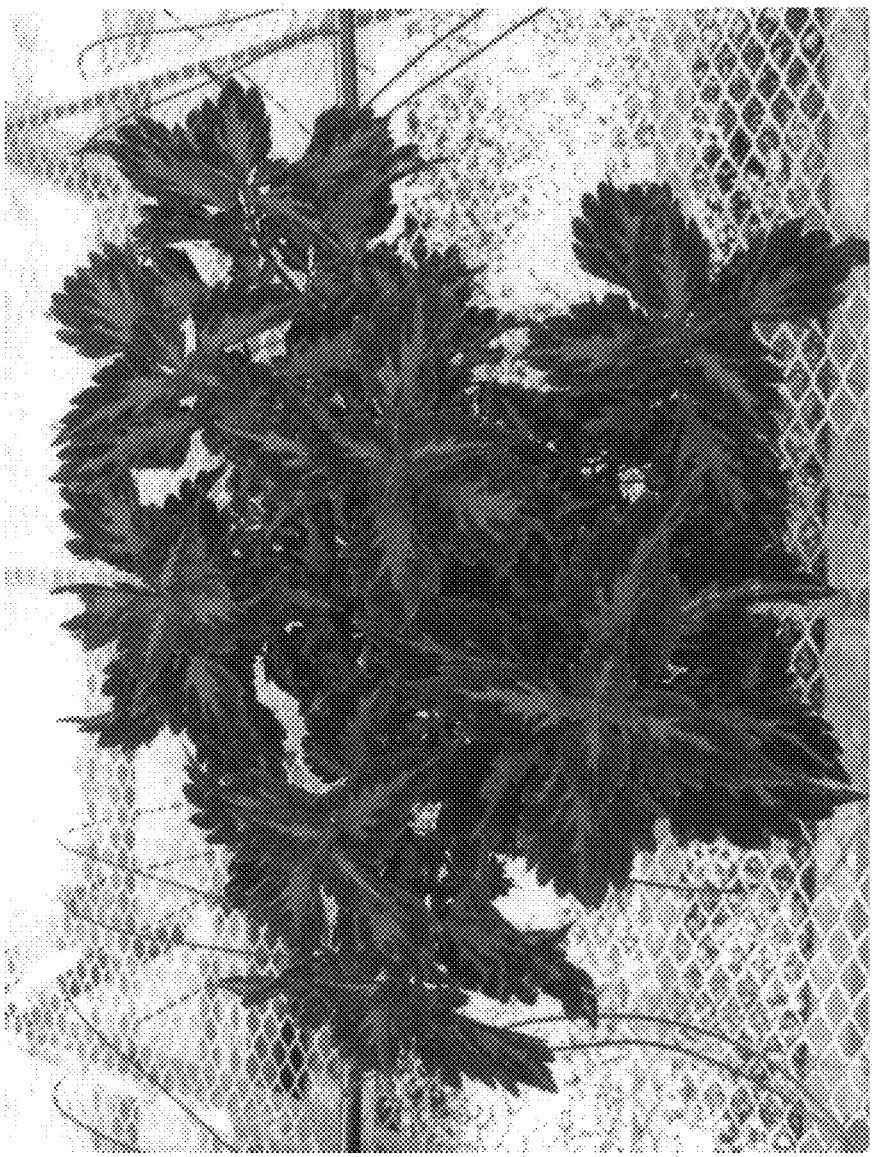
FIG. 2—Shows the growth habit, form, and foliage of 'UF16-88-9.'
Figure 3:
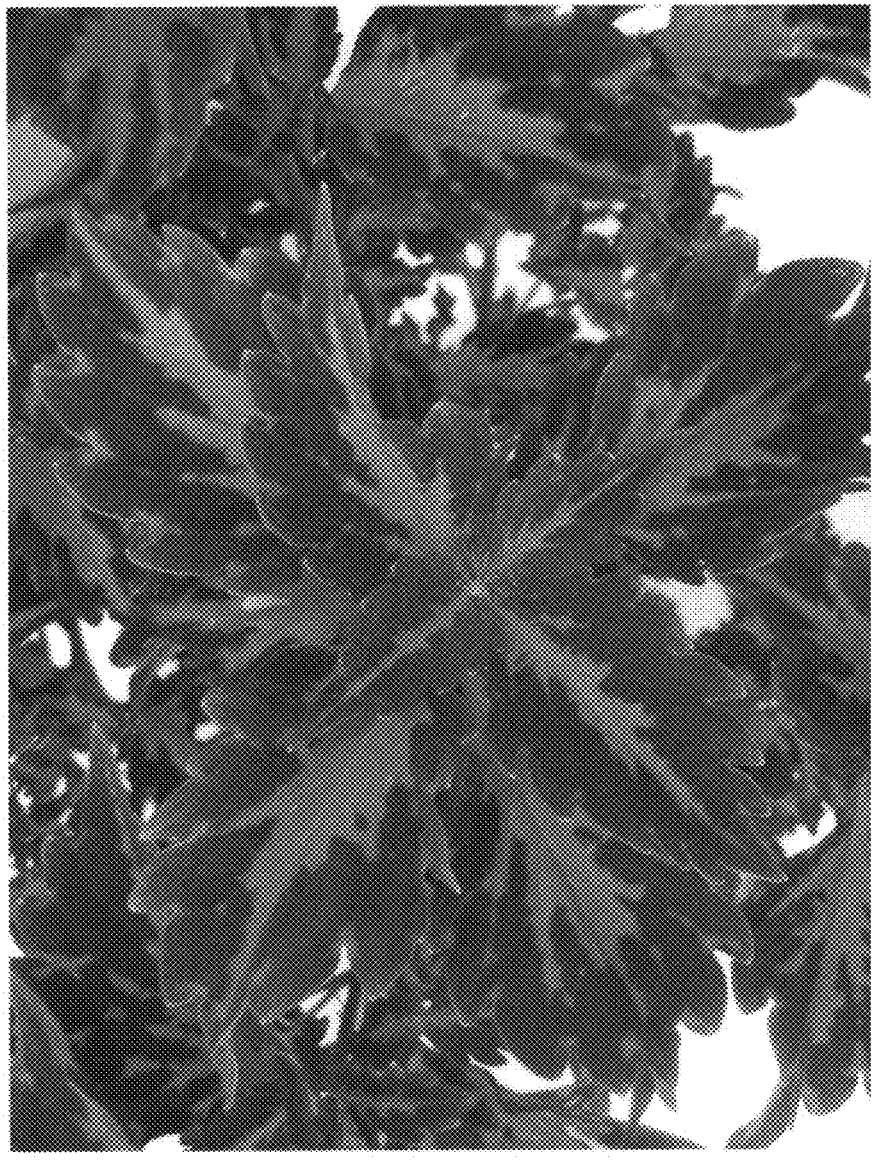
FIG. 3—shows a close-up of the foliage of 'UF16-88-9.'

The following detailed description sets forth the distinctive characteristics of 'UF16-88-9'. The detailed description was obtained using 10-week-old plants grown from unrooted cuttings in May-July 2017 in a poly-covered plastic greenhouse in Gainesville, Fla. The plants were propagated in mist for 10 days after cuttings were stuck and then grown in 1-gallon pots for approximately 9.5 additional weeks. Color references are to The R.H.S. Colour Chart of The Royal Horticultural Society of London (R.H.S.), 2007 5th Edition.

Classification:

*Family*.—Lamiaceae.

*Botanical*.—*Plectranthus scutellarioides*.

*Common name*.—*Coleus*.

*Cultivar name*.—'UF16-88-9'.

Plant description:

*Form*.—Spreading.

*Habit*.—Upright.

*Height* (*from top of soil*).—30-35 cm.

*Width* (*horizontal plant diameter*).—55-60 cm.

Propagation:

*Type cuttings*.—Vegetative meristems having at least 1 node.

*Time to initiate roots*.—3-4 days.

*Time to produce a rooted cutting*.—7-10 days.

*Root habit*.—Fibrous.

*Root description*.—Callus forms in 2 to 3 days, roots initiate in 3-4 days and become a highly branched cutting in 7-10 days.

Branches:

*Quantity per plant*.—10-11.

*Branch color*.—RHS 59B.

*Texture*.—Smooth.

*Pubescence*.—Not present.

*Stem description*.—Square-shaped stem, 0.7 cm in diameter at the soil line.

*Branch diameter*.—0.4-0.5 cm at the base of a 27 cm long branch.

*Branch length*.—25-28 cm.

*Internode length*.—5-6 cm.

*Anthocyanin*.—Not present.

Leaves:

*Quantity of leaves per branch*.—18-20.

*Arrangement*.—Opposite.

*Fragrance*.—Not fragrant.

*Shape*.—Ovate.

*Length*.—10-12 cm.

*Width*.—7-8 cm.

*Apex*.—Broadly acute.

*Base*.—Attenuate and Oblique.

*Margin*.—Lobed.

*Leaf texture* (*both surfaces*).—Smooth.

*Pubescence color* (*both surfaces*).—Not present.

*Venation color*.—Upper surface: Center: RHS 64A. Lower surface: RHS 75A.

*Venation pattern*.—Upper surface: Arcuate. Lower surface: Reticulate.

*Color*.—Immature leaf: Upper surface: Center=RHS 64B; Margin=RHS N79A. Lower surface: Center=RHS 60C; Margin=RHS N79B.

*Color*.—Mature leaf: Upper surface: Center=RHS 64B; Margin=RHS N79A. Lower surface: Center=RHS 60C; Margin=RHS N79B.

*Petiole length*.—3-4 cm.

*Petiole diameter*.—0.2-0.3 cm.

*Petiole color*.—RHS 64A.

*Petiole texture*.—Smooth, no pubescence.

Flowers and seeds: Flowers and seeds have not been observed to date during formal trials in Gainesville, Fla.

Fruit/seed set: Fruit/seed not observed.

Disease and insect resistance: Disease and insect resistance is typical of the species, and thus no claims are made of any superior disease or insect resistance with this cultivar. The most common insect pests observed on this plant in Gainesville, Fla. have been long-tailed or citrus mealybugs (*Pseudococcus* sp.), which occur on older stock plant material held in the greenhouse for over 3-4 months. Impatiens Necrotic Spot Virus (*Bunyaviridae*) has also been observed in plants confined in greenhouses with mixed crops (peppers) infected with Western flower thrips (*Frankliniella occidentalis*). The most common pathogen of this species in the U.S. is downy mildew (*Peronospora lamii*). This pathogen has been observed in stock materials grown closely together in cooler growing seasons.

What is claimed is:

1. A new and distinct *Plectranthus scutellarioides* plant called 'UF16-88-9' as shown and described herein.

* * * * *